US010818163B2

(12) United States Patent
Huster

(10) Patent No.: US 10,818,163 B2
(45) Date of Patent: Oct. 27, 2020

(54) PATIENT CARE SYSTEM AND AN OCCUPANT SUPPORT AND OCCUPANT WEARABLE ITEM USEABLE WITH THE SYSTEM

(71) Applicant: Hill-Rom Services, Inc., Batesville, IN (US)

(72) Inventor: Keith A. Huster, Sunman, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 654 days.

(21) Appl. No.: 13/772,739

(22) Filed: Feb. 21, 2013

(65) Prior Publication Data

US 2014/0232551 A1 Aug. 21, 2014

Related U.S. Application Data

(60) Provisional application No. 61/765,297, filed on Feb. 15, 2013.

(51) Int. Cl.
*G08C 17/02* (2006.01)
*G08C 17/00* (2006.01)
(Continued)

(52) U.S. Cl.
CPC .............. *G08C 17/00* (2013.01); *G08C 17/02* (2013.01); *H02J 50/05* (2016.02); *H02J 50/10* (2016.02);
(Continued)

(58) Field of Classification Search
CPC .............. G06F 19/3406; G06F 19/3418; G06F 19/322; G06F 19/30; G06K 2017/009;
(Continued)

(56) References Cited

U.S. PATENT DOCUMENTS 4,747,413 A * 5/1988 Bloch ..................... A41B 13/00
128/903
5,561,412 A * 10/1996 Novak et al. ............ 340/286.07
(Continued)

FOREIGN PATENT DOCUMENTS

WO 2007050650 A2 5/2007

OTHER PUBLICATIONS

Ultra-Wearable Capacitive Coupled and Common Electrode-Free ECG Monitoring System; Tomas Komensky, Michal Jurcisin, Kornel Ruman, Ondrej Kovac, Daniel Laqua, Peter Husar, Senior Member, IEEE; 34th Annual International Conference of the IEEE EMBS; San Diego, CA; Aug. 28-Sep. 1, 2013.

*Primary Examiner* — Nay Tun
(74) *Attorney, Agent, or Firm* — Barnes & Thornburg LLP

(57) ABSTRACT

A patient care system described herein includes a first electromagnetic coupler associated with the patient, at least one patient-centric appliance in communication with the first coupler, and an occupant support for supporting the patient. The occupant support has a second electromagnetic coupler associated therewith. At least one of the couplers is connectable to an electrical energy source for energizing the coupler. The first and second couplers form a noncontact electromagnetic coupling. An occupant wearable item and an occupant support, both of which are useable with the patient care system, are also described.

17 Claims, 3 Drawing Sheets

(51) Int. Cl.
*H02J 50/10* (2016.01)
*H02J 50/05* (2016.01)
*H04B 5/00* (2006.01)
*A61B 5/00* (2006.01)
*A61B 5/0205* (2006.01)

(52) U.S. Cl.
CPC ......... *H04B 5/0012* (2013.01); *H04B 5/0031* (2013.01); *H04B 5/0037* (2013.01); *H04B 5/0075* (2013.01); *A61B 5/0002* (2013.01); *A61B 5/0205* (2013.01); *A61B 5/681* (2013.01); *A61B 5/6804* (2013.01); *A61B 5/6831* (2013.01); *G08C 2201/30* (2013.01)

(58) Field of Classification Search
CPC .............. G06K 19/0717; A61G 12/001; A61G 2205/60; A61G 7/05; A61G 7/1065; A61G 2203/70; A61G 7/002; A61G 7/005; A61G 7/015; A61G 7/018; A61J 2205/60; A61B 19/44; A61B 5/1113
USPC ..... 340/539.12, 870.3, 870.31, 573.1, 573.7; 600/300; 128/903
See application file for complete search history.

(56) References Cited

U.S. PATENT DOCUMENTS

| | | | |
|---|---|---|---|
| 5,838,223 A * | 11/1998 | Gallant et al. ........... 340/286.07 | |
| 7,722,375 B2 | 5/2010 | Hagen et al. | |
| 7,868,740 B2 | 1/2011 | McNeely et al. | |
| 8,031,080 B2 | 10/2011 | Price et al. | |
| 8,032,199 B2 | 10/2011 | Linti et al. | |
| 8,074,389 B2 * | 12/2011 | Greer ...................... G09F 3/005 283/75 | |
| 8,804,622 B1 * | 8/2014 | Thai et al. .................... 370/328 | |
| 2001/0054005 A1 * | 12/2001 | Hook et al. ..................... 705/20 | |
| 2004/0193020 A1 * | 9/2004 | Chiba et al. .................. 600/300 | |
| 2005/0034485 A1 * | 2/2005 | Klefstad-Sillonville .................... A41D 13/1281 66/171 | |
| 2005/0182305 A1 * | 8/2005 | Hendrich ................. A61B 5/00 600/300 | |
| 2006/0006999 A1 * | 1/2006 | Walczyk et al. ......... 340/539.27 | |
| 2006/0025696 A1 * | 2/2006 | Kurzweil et al. ............. 600/509 | |
| 2006/0066449 A1 * | 3/2006 | Johnson .................. 340/539.12 | |
| 2007/0032733 A1 * | 2/2007 | Burton ............... A61B 5/02405 600/509 | |
| 2008/0147442 A1 * | 6/2008 | Warner et al. ..................... 705/3 | |
| 2009/0048556 A1 * | 2/2009 | Durand ......................... 604/20 | |
| 2010/0132237 A1 * | 6/2010 | McDermott ........... G09F 3/005 40/633 | |
| 2011/0025817 A1 * | 2/2011 | Carter .................... A61B 5/1112 348/14.02 | |
| 2011/0105861 A1 * | 5/2011 | Derchak ............... A61B 5/0816 600/301 | |
| 2011/0112793 A1 * | 5/2011 | Diebold .................... A61B 5/11 702/141 | |
| 2011/0248672 A1 * | 10/2011 | Herman et al. ................ 320/108 | |
| 2012/0101411 A1 * | 4/2012 | Hausdorff ............. A61B 5/1117 600/595 | |
| 2012/0158074 A1 * | 6/2012 | Hall ....................... A61B 5/024 607/5 | |
| 2012/0191038 A1 * | 7/2012 | Gerber ............................ 604/67 | |
| 2012/0312196 A1 * | 12/2012 | Newkirk ......................... 108/23 | |
| 2013/0127620 A1 * | 5/2013 | Siebers .................. G08B 21/02 340/573.1 | |
| 2013/0131617 A1 * | 5/2013 | Kovensky .......... A41D 13/1281 604/327 | |
| 2014/0022079 A1 * | 1/2014 | Wilson ................. G06F 19/327 340/573.1 | |

\* cited by examiner

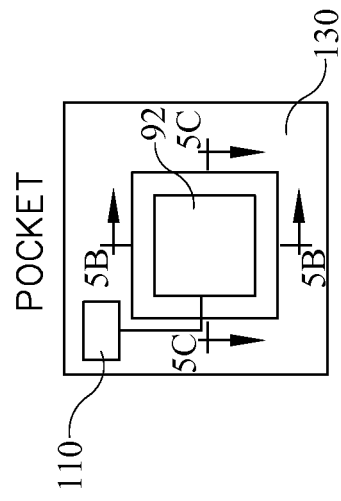
FIG. 5A
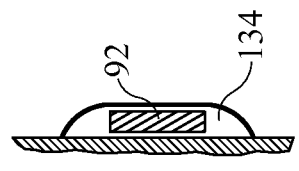
FIG. 5C
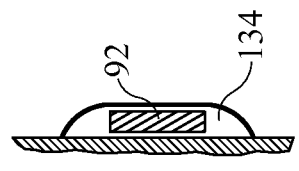
FIG. 5B
FIG. 4A
FIG. 4B
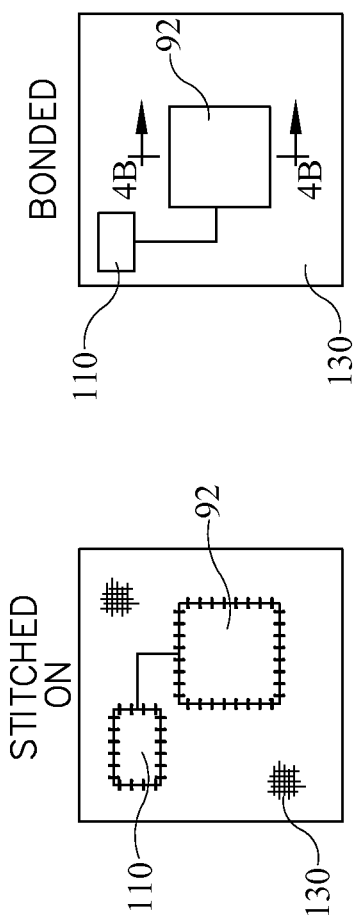
FIG. 3

PATIENT CARE SYSTEM AND AN OCCUPANT SUPPORT AND OCCUPANT WEARABLE ITEM USEABLE WITH THE SYSTEM

TECHNICAL FIELD

The subject matter described herein relates to a system for care of a patient in a setting such as a hospital, an occupant support useable with the system, and a patient wearable item useable with the system, in particular a system, occupant support, and wearable item adapted to establish a noncontact electromagnetic coupling for the conveyance of information, noninformational electrical energy or both.

BACKGROUND

Settings for the care of sick or injured patients include both professionally operated facilities and home care settings. Such settings include an occupant support such as a bed for the patient to occupy during his or her recovery. Many styles of beds include features and systems to enhance patient comfort, safety, and recovery and to assist caregivers in attending to the patient's needs. Some of these features are adjustable so that the bed can be configured to take on a particular state consistent with the best interests of a specific patient. Examples of such features include frames that are adjustable in elevation and/or angular orientation, deck sections supported by the frame that are orientation adjustable relative to the frame, mattresses having bladders that can be adjusted to different degrees of firmness, and patient position monitoring (PPM) systems for monitoring patient motion and position. An example of a bed state that may be suitable for a patient known to be at risk of falling is a "fall-safe" state in which the frame is at its lowest possible elevation and/or the PPM system is armed to alert caregivers to patient activity consistent with a patient's attempt to exit the bed. An example of a bed state that may be suitable for a patient at risk of developing pressure ulcers is a "roll state" that slowly inflates and deflates a pair of mattress bladders out of phase with each other to gently roll the patient from side to side. Some bed states may be thought of as preemptive states by reason of being based on information that is not likely to change abruptly (e.g. fall risk or pressure ulcer risk). Other bed states may be thought of as reactive states because they are used in response to information that may change abruptly. An example of a reactive state is a cardiopulmonary resuscitation (CPR) state put in effect if the patient's physiological readings change from expected values to values suggestive of the need for CPR. Assuming the bed is not already in a CPR state, transitioning the bed to the CPR state involves placing all the deck sections in a coplanar orientation, raising the frame to a height suitable for a caregiver to apply CPR and, if the bed is equipped with an inflatable mattress, inflating the mattress sufficiently to support the patient during CPR rather than allowing the patient to sink into the mattress.

It may be beneficial for certain information about the patient to be conveyed to systems or devices onboard the bed. For example information that the patient is at risk of falling can be used to place the bed in the fall-safe state and/or used to disable bed controls that would allow the patient to place the bed in a state other than the fall-safe state. In another example, information that a patient is at risk of developing pressure ulcers can be used to activate the above described roll state. In another example, information from physiological sensors can be used to reconfigure the bed from its existing state to a CPR state so that CPR efforts can begin without delay once a caregiver arrives at the bedside. In yet another example patient identity information encoded on a wristband worn by the patient may be conveyed to the bed which, in turn, communicates with an electronic medical record (EMR) database to acquire patient specific information.

It may also be beneficial for certain information from the bed to be conveyed to a patient-centric device or appliance. As used herein a patient-centric device or appliance is one that, over a given interval of time, is associated with a single patient even though the appliance may be a reusable appliance that can be associated with a first patient during a first time interval and with a second patient during a second time interval. In addition, a patient-centric appliance is one that takes on patient specific states or observes patient specific limits. One example is a physiological sensor such as a blood pressure sensor, a heart rate sensor, a body temperature sensor, a skin temperature sensor or a respiration rate sensor, each of which is responsive to short term changes in the physiological parameter that it detects. Another example is a memory device whose memory contains, for example, an identification code assigned to the patient. Another example is a user interface device that allows the patient to control various bed functions such as deck section orientation or the firmness of an air mattress or to control environmental parameters such as ambient temperature, or to control a nearby radio or television or to issue a nurse call signal to request assistance from a nurse. Another example is a display that has been assigned to a specific patient for displaying information specific to the assigned patient. One example of information conveyance from the bed to a patient-centric device involves a patient gown that includes an information display panel capable of displaying information such as the name of the patient's nurse and/or physician. The bed, after first having obtained that information from the EMR, can convey the information to the display.

It is also beneficial if the information conveyance between the bed and the patient-centric device or appliance is a direct conveyance that does not require the intervention of third party devices or systems. It is also beneficial if electrical energy can be transferred between the bed and a patient-centric device or appliance.

SUMMARY

The present invention may comprise one or more of the features recited in the appended claims and/or one or more of the following features or combinations thereof. A patient care system described herein includes a first electromagnetic coupler associated with the patient, at least one patient-centric appliance in communication with the first coupler, and an occupant support such as a bed for supporting the patient. The occupant support has a second electromagnetic coupler associated therewith. At least one of the couplers is connectable to an electrical energy source for energizing the coupler. The first and second couplers form a noncontact electromagnetic coupling.

An occupant wearable item described herein comprises a substrate, a first electromagnetic coupler bound to the substrate and at least one occupant-centric appliance in communication with the first coupler. The first coupler is adapted to form a noncontact electromagnetic coupling with a second noncontact electromagnetic coupler which is not bound to the substrate.

An occupant support described herein includes a second electromagnetic coupler adapted to form a noncontact electromagnetic coupling with a first electromagnetic coupler associated with an occupant of the occupant support, and a control module adapted to receive information conveyed across the coupling and to issue a signal to configure the occupant support for the occupant in response to the conveyed information.

BRIEF DESCRIPTION OF THE DRAWINGS

The foregoing and other features of the various embodiments of the system, occupant support and occupant wearable item described herein will become more apparent from the following detailed description and the accompanying drawings in which:

FIGS. 3, 4A-4B and 5A-5C are illustrations schematically showing three variants of a patient-centric device or appliance being bound to a patient wearable item such as a garment.

DETAILED DESCRIPTION

Figure 1:
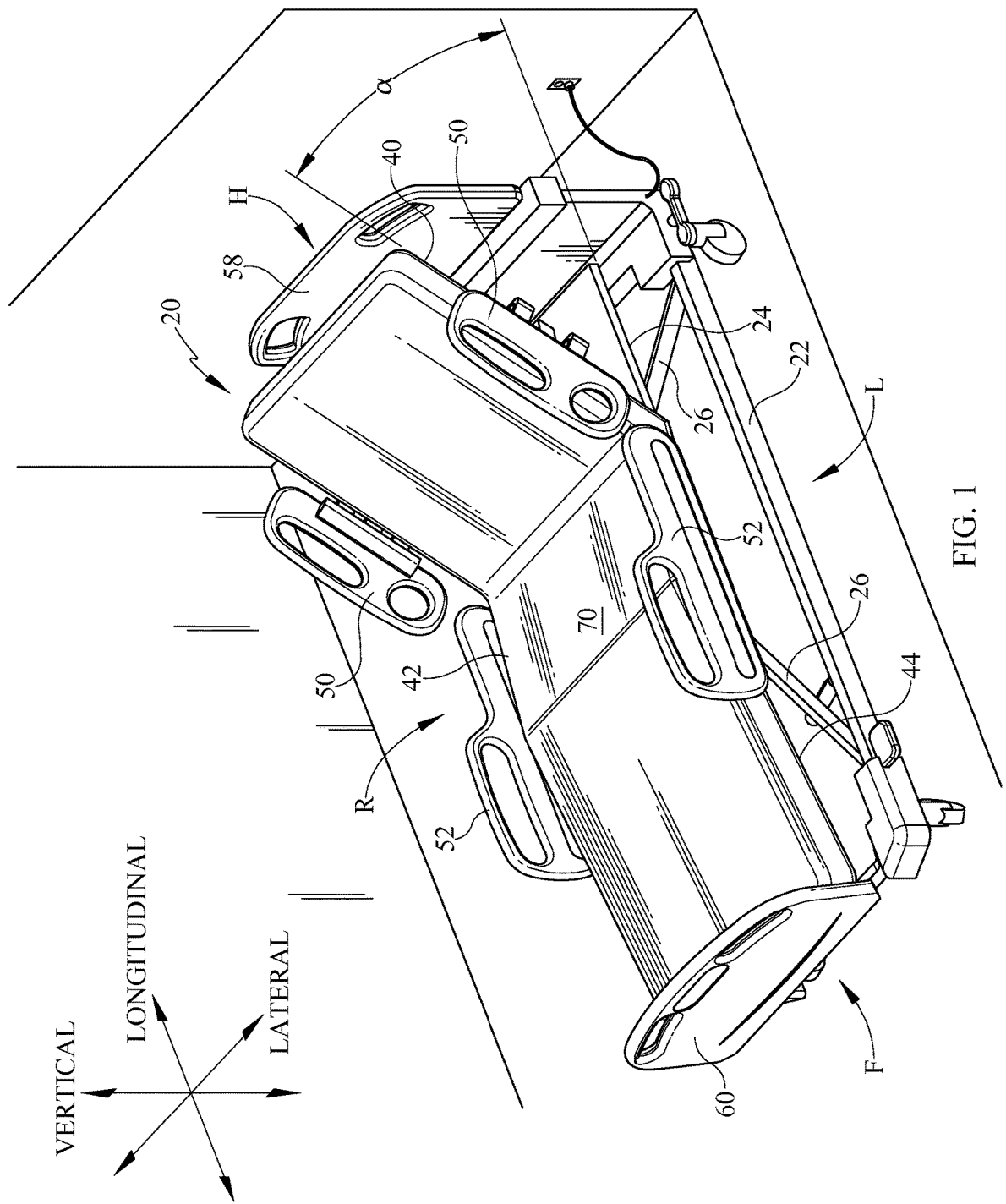
FIG. 1 is a perspective view of a hospital bed.

Referring to FIG. 1 an occupant support exemplified as a hospital bed 20, extends longitudinally from a head end H to a foot end F and laterally from a left side L to a right side R. The bed includes a base frame 22 and an elevatable frame 24 connected to the base frame by head and foot end lift mechanisms represented in the illustration by links 26. The bed also includes a deck comprising a torso section 40, a seat section 42, and a leg section 44. Actuators, not illustrated, are operable to adjust the orientation angles of the deck sections, for example angle α of torso section 40. The bed also includes left and right head end siderails 50 connected to the torso deck section and left and right foot end siderails 52 connected to the elevatable frame. The bed also includes a headboard 58 attached to base frame 22 and a footboard 60 attached to elevatable frame 24. A mattress 70 rests on the deck.

Figure 2:
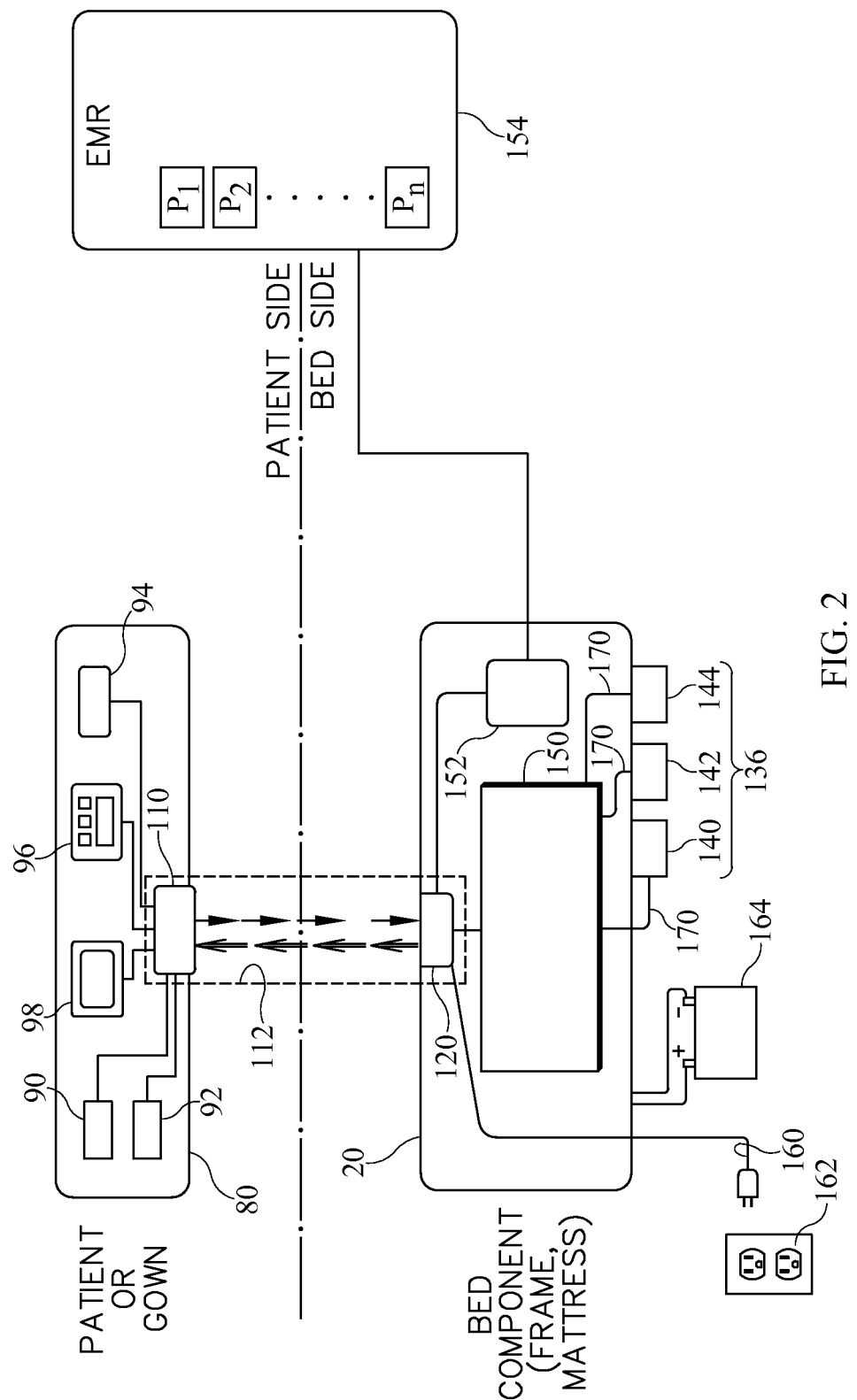
FIG. 2 is a schematic showing a bed, a set of patient-centric devices or appliances, a first noncontact coupler, a second noncontact coupler and a coupling defined by the first and second couplers.

FIG. 2 schematically shows examples of patient-centric devices or appliances all associated with a host 80. As used herein a patient-centric appliance is one that, for a given interval of time, is associated with a single patient even though the appliance may be a reusable appliance that can be associated with a first patient during a first time interval and with a second patient during a second time interval. In addition, a patient-centric appliance is one that takes on patient specific states or observes patient specific limits. One example of a patient-centric appliance is a physiological sensor such as schematically illustrated heart rate sensor 90 or skin temperature sensor 92. Other types of physiological sensors include skin temperature sensors and respiration rate sensors. The sensors of interest are those that are responsive to short term changes in the physiological parameter that they detect as opposed to instruments that detect relatively stable conditions such as broken bones, tumors, and morphological attributes. Such sensors are patient-centric because they sense the physiological parameters of a specific patient. Another example of a patient-centric appliance is a memory device 94 such as a tag whose memory contains, for example, an identification code assigned to the patient. Identification tag 94 is patient-centric because it is encoded with information specific to a designated patient. Another example of a patient-centric appliance is a user interface device 96 that allows the patient to control various bed functions such as the angular orientation of deck sections 40, 42, 44 or the firmness of mattress 70 if the mattress is an inflatable mattress, or to control environmental parameters such as ambient temperature, or to control a nearby radio or television or to issue a nurse call signal to request assistance from a nurse. User interface 96 is patient-centric because it is configurable for the needs of a particular patient. For example if the patient is considered susceptible to accumulations of fluid in his or her lungs, the user interface might be configured to disregard any input thereto that would cause torso deck section 40 to move to an orientation α less than 60°. Another example of a patient-centric appliance is a display 98 that displays information specific to the assigned patient. Display 98 is patient centric because it will display information specific to a designated patient.

The patient-centric appliance may be secured directly to the patient (also referred to as a bed occupant) in which case host 80 of FIG. 2 represents the patient. For example skin temperature sensor 92 might be temporarily attached to the patient's skin by an adhesive or might be held against the patient's skin by an elastic band or a bandage. Alternatively the patient-centric appliance may be a patient wearable item or a component of a patient wearable item, in which case host 80 of FIG. 2 is the patient wearable item. Patient wearable items include garments such as gowns or other sleepwear, and articles such as a wristband that, despite being worn by a patient, is not typically thought of as a garment. In one example host 80 is a hospital gown with patient identification tag 94, display 98, and user interface 96 are appliances sewn into the gown. In another example identification tag 94 is a wristband or a component of a wristband. Although certain types of appliances may be thought of as more suitable for direct, intimate contact with the patient (e.g. the physiological sensors) and other appliances may bethought of as more suitable as a component of a patient wearable item, the foregoing examples are not to be construed as limiting whether the appliances are located exclusively on the patient, located exclusively on the wearable item, or distributed between the patient and the wearable item.

In some cases the patient-centric appliance may be a stand-alone device. For example user interface 96 may be a hand-held remote control user interface assigned to a specific patient during his stay in a health care facility. The patient-centric device could also be a device permanently or removably mounted on the bed such as a user interface permanently or removably mounted on siderail 50 but which is reconfigurable to meet the needs of a specific patient.

FIG. 2 also shows a first electromagnetic coupler 110 associated with the patient and referred to as a patient-side coupler. At least one of the patient-centric appliances is in communication with the first coupler. In FIG. 2 all the appliances are in communication with the first coupler as indicated by the lines extending between the first coupler and each appliance, which lines do not necessarily represent a physical communication pathway such as a wire. The first coupler 110 is adapted to form a noncontact electromagnetic coupling 112 with a second noncontact electromagnetic coupler 120. In the example of FIG. 2 the second coupler is mounted on or otherwise associated with the bed and is therefore referred to as a bed-side coupler (or more generally as an occupant support side coupler). The first and second couplers may be capacitive couplers adapted to form a capacitive coupling with each other so that coupling 112 is a capacitive coupling or may be inductive couplers adapted to form an inductive coupling with each other so that coupling 112 is an inductive coupling.

FIGS. 3-5 show an occupant wearable item such as a gown comprising a substrate 130, which is the material from which the gown is made, a first electromagnetic coupler 110 bound to the substrate and at least one occupant-centric appliance represented by sensor 92 in communication with the first coupler and also bound to the substrate so that both appliance 92 and coupler 110 are components of the gown. Various means may be used for causing the coupler and appliance to be bound to the gown. These include stitching the coupler and appliance to the substrate (FIG. 3), bonding the coupler and appliance to the substrate with an adhesive 132 (FIGS. 4A, 4B), and trapping the coupler in a closed pocket 134 (FIGS. 5A, 5B, 5C). Coupler 110 is configured to form a noncontact electromagnetic coupling 112 with a second noncontact electromagnetic coupler 120 which is not bound to the substrate.

Returning to FIG. 2, the second electromagnetic coupler 120 is mounted on or otherwise associated with bed 20. The bed also includes effectors indicated collectively as feature 136 for changing the state or configuration of the bed. Examples of effectors include frame actuators 140 for changing the elevation of elevatable frame 24, deck section actuators 142 for changing the angular orientation of deck sections 40, 42, 44, and a blower 144 for supplying pressurized air to the bladders of an inflatable mattress. The bed also includes a bed control module 150 which is a circuit board having electrical circuitry which governs operation of the effectors. The bed also includes a communication module 152 adapted to communicate with a patient nonspecific database such as an electronic medical record (EMR) database which contains individual patient records P1, P2. In practice the communication module establishes communication with database 154 to retrieve patient specific information contained in one of the records, in particular the record of the patient assigned to the bed.

The bed also includes a power cord 160 for connecting the electrical components of the bed to an electrical outlet 162 and may include a battery 164 to enable operation of the electrical components during power outages or when the bed is not near an outlet or is being moved from one location to another.

At least one of first and second couplers 110, 120 is connectable to an electrical energy source for energizing the coupler. The first and second couplers form a noncontact electromagnetic coupling 112 such as the capacitive or inductive coupling already mentioned. Components such as first coupler 110 and appliances 90, 92, 94, 96, 98 may be referred to as patient-side components. Components such as second coupler 120, bed 20, bed control module 150 and communication module 152 may be referred to as bed-side components. The dash-dot line extending across FIG. 2 differentiates between the patient-side components and the bed-side components.

Electromagnetic coupling 112 is adapted to convey noninformational electrical energy, information, or both between the bed-side components and the patient side components. Both the bed-side and the patient side can be the origin and/or the destination for the conveyed information or noninformational electrical energy. In one example coupling 112 is used to inductively transfer electrical energy originating on the bed-side (e.g. from outlet 162) to the patient side in order to operate one or more of the patient-side appliances 90, 92, 94, 96, 98. In another example a signal having informational content can be superimposed on the electromagnetic field that couples the bed-side to the patient side. One example of such a signal is a signal that encodes a patient identification number or other patient specific information obtained by communication module 152 from the EMR 154 and conveyed across coupling 112 so that the identification number and patient specific information can be written to identification tag 94 on the patient side of coupling 112. In another example an informational signal whose energy content is inadequate to properly operate a device on the destination side of the coupling may be conveyed across the coupling 112. One example of such a signal is a signal from one of the physiological sensors 90, 92.

As noted above the bed-side and the patient side are both eligible to be the origin and/or the destination for the conveyed information or noninformational electrical energy. In practice it is expected that only the bed-side (i.e. second) coupler 120 will be connected to a source of electrical energy capable of operating devices on the patient-side. Conversely it is expected that patient side coupler 110 will not be connected to a source of electrical energy or, if so connected, will be connected to a source of electrical energy unsuitable for operating devices on the bed-side of coupling 112. In such an architecture the coupling will serve to convey noninformational electrical energy, information, or both from the bed-side to the patient side, but, as a practical matter, will serve to convey only information from the patient-side to the bed-side. To the extent that the coupling conveys noninformational electric energy, the energy will not play any meaningful role in operating devices on the bed-side.

A patient care system based on the foregoing includes the first electromagnetic coupler 110 associated with the patient and at least one appliance such as sensor 90, sensor 92, display 96, user interface 98 or identifier tag 94 in communication with the first coupler. The patient care system also includes second electromagnetic coupler 120 adapted to form a noncontact electromagnetic coupling with the first electromagnetic coupler, and bed control module 150. Bed control module 150 is adapted to receive information conveyed across the coupling and to issue a signal 170 to configure the bed for the occupant in response to the conveyed information. In one example the conveyed information is information from tag 94 indicating that the patient assigned to the bed has a high risk of falling, and the issued signal is one that commands a change in the state of the bed from its existing state to a fall-safe state. Alternatively or additionally, signal 170 may be one that reflects a constraint on an otherwise achievable state of the bed. For example signal 170 as received by frame actuator 140 may, for most patients, be a "full authority" signal such that the elevation of elevatable frame 24 is not subject to any patient specific constraints, but for a fall-risk patient is a null signal that prohibits elevation of frame 24 to an elevation higher than its minimum elevation or a signal that imposes constraints on the achievable elevation.

The following examples will serve to elucidate the features and operation of the patient care system, occupant (patient) wearable item and bed.

Example 1

A member of a hospital admissions staff recognizes that a patient being admitted to the hospital is a "fall-risk" patient, i.e. is highly likely to fall. The staff member indicates the fall risk status in the patient's record (e.g. P1 of EMR database 154), produces a wristband 94 containing an identifying number unique to the patient, and places the wristband on the patient's wrist. The patient, upon arriving at her bed 20 removes her clothing in exchange for a hospital gown 80 with a first coupler 110 bound thereto. Upon occupying the bed, a noncontact electromagnetic communication link is established (i.e. coupling 112). The patient's identification number is conveyed across the coupling to communication module 152 which interrogates patient record P1. The fact that the patient is a fall risk patient is communicated to the bed control module which commands appropriate effectors 136 to place the bed in a "fall-safe" state.

Example 2

Example 2 is the same as example 1 except that the admissions staffer encodes the patient's identifying number on a tag 94 which is later attached to a gown or which is pre-attached to a gown.

Example 3

Example 3 is the same as examples 1 and 2 except that in addition to the bed being placed in a fall-safe state, user interface is configured to disregard any patient originated command that would take the bed out of the fall-safe state. In addition, display 98 is reconfigured to display a code which reveals the patient's fall-risk status to the caregiver staff.

Example 4

Example 4 is the same as the previous examples except that noninformational electrical energy which originates at outlet 162 or battery 164 and which is sufficient to operate any of appliances 90, 92, 94, 96, 98 that require electrical energy is conveyed across coupling 112.

Example 5

A patient's vital signs, which are monitored by physiological sensors, undergo a change consistent with a cardiac event which may require cardiopulmonary resuscitation. The physiological data is conveyed across coupling 112 to bed control module 150. The bed control module commands the effectors 136 to place the bed in its CPR configuration so that the bed is already in an optimum state for CPR when caregivers arrive at the bed.

Although this disclosure refers to specific embodiments, it will be understood by those skilled in the art that various changes in form and detail may be made without departing from the subject matter set forth in the accompanying claims.

I claim:

1. A patient care system comprising:
   a first electromagnetic coupler associated with a specific patient;
   at least one patient-centric appliance in communication with the first electromagnetic coupler;
   a patient wearable garment which hosts the patient-centric appliance and the first coupler; and
   an occupant support for supporting the patient, the occupant support having a second electromagnetic coupler associated therewith, at least one of the electromagnetic couplers being connectable to an electrical energy source for energizing the respective electromagnetic coupler, the first and second electromagnetic couplers forming a noncontact electromagnetic coupling;
   wherein only the second electromagnetic coupler is connectable to the electrical energy source and the electromagnetic coupling conveys noninformational electrical energy from the occupant support to the first electromagnetic coupler and the noninformational electrical energy operates the at least one patient-centric appliance,
   wherein the patient-centric appliance includes a physiological sensor, and
   wherein the patient-centric appliance is operable to receive patient specific information from a patient record in a patient nonspecific database that is remote from the patient-centric appliance and to display the patient specific information received from the patient nonspecific database, the displayed information including a risk factor associated with the specific patient.

2. The system of claim 1 wherein the couplers are capacitive couplers and form a capacitive coupling.

3. The system of claim 1 wherein the couplers are inductive couplers and form an inductive coupling.

4. The system of claim 1 including a communication module adapted to communicate with the patient nonspecific database to retrieve patient specific information.

5. The system of claim 4 wherein the communication module is a component of the occupant support.

6. The patient care system of claim 1, wherein the patient wearable garment is a hospital gown and the patient-centric appliance is a component of the gown.

7. The patient care system of claim 6, wherein the patient-centric appliance is stitched to a substrate of the gown.

8. The patient care system of claim 6, wherein the patient-centric appliance is trapped within a closed pocket of the gown.

9. The patient care system of claim 1, wherein the patient-centric appliance is trapped within a closed pocket of the patient wearable garment.

10. The patient care system of claim 1, wherein the patient wearable garment is a hospital gown and the first coupler is a component of the gown.

11. The patient care system of claim 10, wherein the first coupler is stitched to a substrate of the gown.

12. The patient care system of claim 10, wherein the first coupler is trapped within a closed pocket of the gown.

13. The patient care system of claim 10, wherein the first coupler is adhered to the gown.

14. The patient care system of claim 1, wherein the patient-centric appliance obtains information from the occupant support.

15. The patient care system of claim 1, wherein the occupant support obtains information from an electronic medical record database.

16. The patient care system of claim 15, wherein the occupant support obtains information from an electronic medical record database through a direct conveyance.

17. The patient care system of claim 1, wherein the patient-centric appliance displays a code which reveals the specific patient's fall-risk status.

* * * * *